United States Patent
Barral et al.

(10) Patent No.: US 11,464,582 B1
(45) Date of Patent: *Oct. 11, 2022

(54) SURGERY GUIDANCE SYSTEM

(71) Applicant: Verily Life Sciences LLC, South San Francisco, CA (US)

(72) Inventors: Joëlle K. Barral, Mountain View, CA (US); Blake Hannaford, Seattle, WA (US); Eden Rephaeli, Oakland, CA (US); Christine Denise Ching, Palo Alto, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 16/835,105

(22) Filed: Mar. 30, 2020

Related U.S. Application Data

(63) Continuation of application No. 14/536,271, filed on Nov. 7, 2014, now Pat. No. 10,639,104.

(51) Int. Cl.
*A61B 34/20* (2016.01)
*A61B 1/04* (2006.01)
*A61B 34/00* (2016.01)
*A61B 90/00* (2016.01)
*A61B 90/50* (2016.01)

(52) U.S. Cl.
CPC .............. *A61B 34/20* (2016.02); *A61B 1/04* (2013.01); *A61B 34/25* (2016.02); *A61B 90/50* (2016.02); *A61B 2034/2057* (2016.02); *A61B 2034/2074* (2016.02); *A61B 2034/252* (2016.02); *A61B 2090/366* (2016.02); *A61B 2090/376* (2016.02); *A61B 2090/378* (2016.02); *A61B 2090/502* (2016.02)

(58) Field of Classification Search
CPC ........... A61B 34/20; A61B 1/04; A61B 34/25; A61B 90/50; A61B 2034/2057; A61B 2034/2074; A61B 2034/252; A61B 2090/366; A61B 2090/376; A61B 2090/378; A61B 2090/502
See application file for complete search history.

(56) References Cited

U.S. PATENT DOCUMENTS

| | | |
|---|---|---|
| 8,169,696 B2 | 5/2012 | Yazdanfar et al. |
| 2006/0281971 A1 | 12/2006 | Sauer |
| 2007/0060984 A1 | 3/2007 | Webb |

(Continued)

OTHER PUBLICATIONS

Wikipedia, the free encyclopedia, "Image-guided surgery", http://en.wikipedia.org/wiki/Image-guided_surgery, Last accessed Oct. 20, 2014, 2 pages.

(Continued)

*Primary Examiner* — Bo Joseph Peng
(74) *Attorney, Agent, or Firm* — Christensen O'Connor Johnson Kindness PLLC

(57) ABSTRACT

Image guided surgery includes capturing a primary modality image of a surgical field of a patient with a camera system, obtaining a secondary modality image of the surgical field registered to the primary image, generating a surgical guidance image based at least in part upon the secondary modality image, and projecting the surgical guidance image onto the patient. The surgical guidance image presents visual augmentations on or over the patient to inform a medical practitioner during a surgical procedure.

10 Claims, 6 Drawing Sheets

(56) References Cited

U.S. PATENT DOCUMENTS

| | | | |
|---|---|---|---|
| 2009/0080737 A1* | 3/2009 | Battle | A61M 25/0662 |
| | | | 382/131 |
| 2011/0069159 A1 | 3/2011 | Soler | |
| 2011/0105895 A1 | 5/2011 | Kornblau | |
| 2011/0117025 A1 | 5/2011 | Dacosta et al. | |
| 2013/0041266 A1* | 2/2013 | Rockrohr | A61B 90/39 |
| | | | 600/407 |
| 2013/0218024 A1* | 8/2013 | Boctor | A61B 6/4441 |
| | | | 600/476 |
| 2014/0022283 A1 | 1/2014 | Chan | |
| 2014/0187967 A1 | 7/2014 | Wood et al. | |
| 2014/0276008 A1 | 9/2014 | Steinbach et al. | |
| 2016/0000515 A1 | 1/2016 | Sela | |
| 2017/0042631 A1 | 2/2017 | Doo | |

OTHER PUBLICATIONS

Wikipedia, the free encyclopedia, "Fluorescence image-guided surgery", http://en.wikipedia.org/wiki/Fluorescence_image-guided_surgery, Last accessed Oct. 20, 2014, 4 pages.

Wikipedia, the free encyclopedia, "Endoscopy", http://en.wikipedia.org/wiki/Endoscopy, Last accessed Oct. 20, 2014, 7 pages.

Wikipedia, the free encyclopedia, "Laparoscopic surgery", http://en.wikipedia.org/wiki/Laparoscopic_surgery, Last accessed Oct. 20, 2014, 8 pages.

"UNO Laparoscopic Visualization Research", Augmented Reality Technology, University of North Carolina at Chapel Hill, Aug. 11, 1998, http://www.cs.unc.edu/Research/us/laparo.html, Last accessed Nov. 4, 2014, 4 pages.

\* cited by examiner

_US 11,464,582 B1_

SURGERY GUIDANCE SYSTEM

CROSS REFERENCE TO RELATED APPLICATIONS

This application is a continuation of U.S. patent application Ser. No. 14/536,271, filed Nov. 7, 2014, the entirety of which is incorporated by reference herein for all purposes.

TECHNICAL FIELD

This disclosure relates generally to medical devices, and in particular, relates to image-guided surgery systems.

BACKGROUND INFORMATION

Image-guided surgery ("IGS") employs pre-operative and/or intraoperative images to guide a surgeon during a surgical procedure. Laparoscopy and thoracoscopy are examples of IGS. Laparoscopy is a surgical procedure performed in the abdomen or pelvis through one or several small incisions with the aid of a camera. Thoracoscopy is a surgical procedure performed within the thoracic cavity (chest). These procedures collectively are referred to as endoscopy, which includes the use of an endoscope inserted into the body to examine the interior of the patient with minimal invasiveness. The endoscope includes a camera to acquire real time images of the operative field and may include additional instrumentation to biopsy, cut, ablate, cauterize, or otherwise manipulate a surgical target.

Another example of IGS is fluorescence IGS ("FIGS"), which uses fluorescent emission to image and guide a surgical procedure. FIGS may be used in endoscopy or open cavity surgical procedures. During FIGS, a fluorescent dye is introduced into the patient (e.g., intravenously, orally, locally) either prior to or during the surgical procedure. A particular fluorescent dye may be used, which preferentially selects cancerous cells or other anatomical structures and fluorescently labels these anatomical targets. The fluorescence image is captured by a fluorescence camera and referenced by the surgeon to identify one or more surgical targets of interest or anatomical structures. In some instances, the fluorescence image is presented with an RGB image, either adjacent to or overlaid, to provide the surgeon with additional visual information of the operative field. These RGB images can be real time images or preoperative images.

Conventional IGS systems, including those described above, present the real time images of the operative field to the surgeon on a screen, such as a liquid crystal display ("LCD") monitor. The screen is usually placed above the patient and the surgeon has to either constantly look up and down between the surgical field and the screen, or work exclusively off the screen. Looking up is distracting, disorientating, and time consuming. This configuration is suboptimal as it hinders acute reaction to deleterious events only visible on the screen and the surgeon must translate or guess where a fluorescence target is actually located relative to his hands and surgical instruments.

If both the RGB and fluorescence images are presented on the screen, the surgeon's perception of the operation is changed. Surgeons performing open operative procedures are used to looking at their hands directly. In addition, the position of the screen is typically optimized for viewing by the surgeon, whereas the rest of the surgical team may have a poor viewing angle or no line-of-sight to check what the surgeon is doing or anticipate his next move. In addition, none of the conventional techniques are ergonomically optimized, often resulting in neck and back pain for the surgeon.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Figure 1:
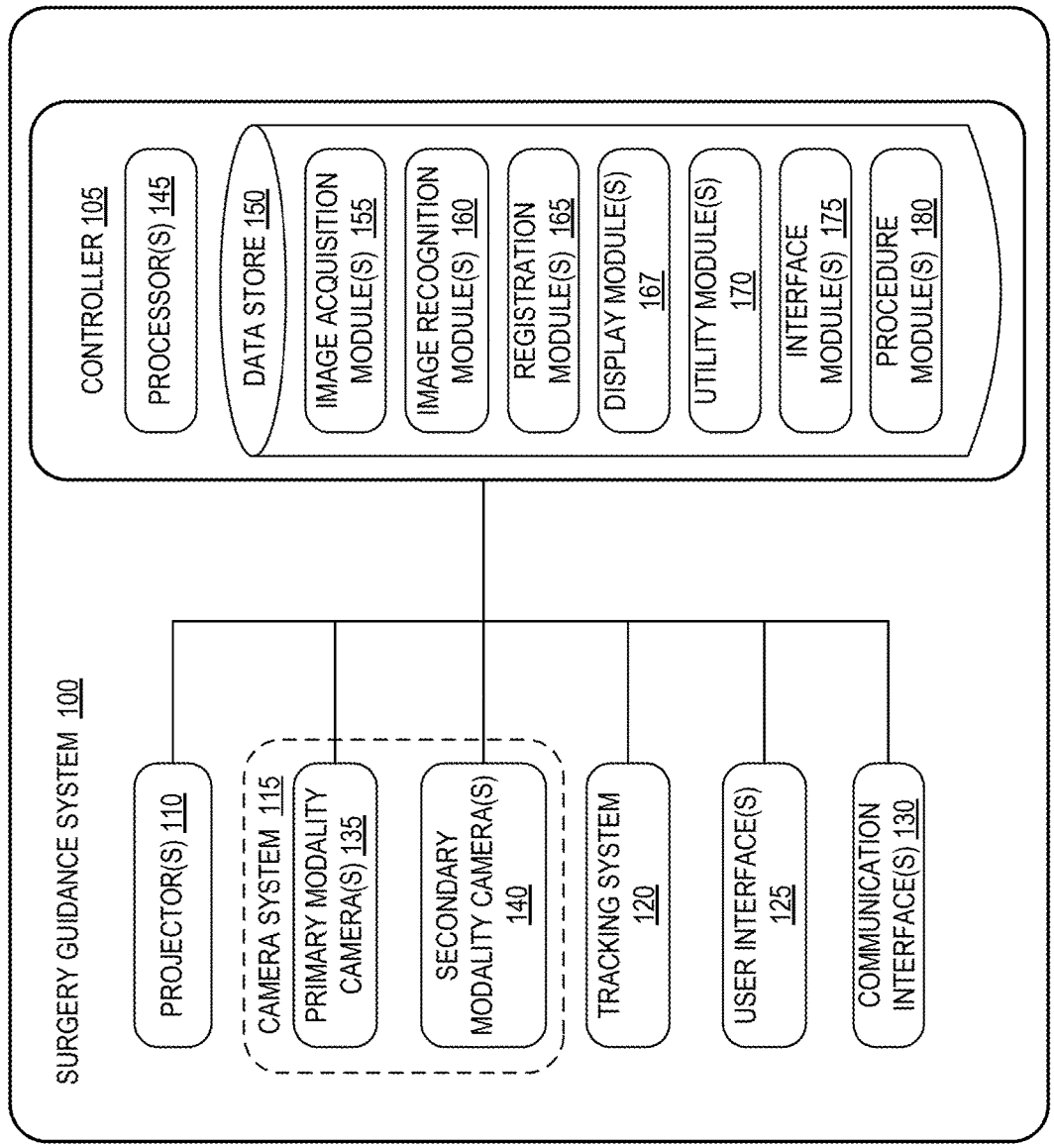
FIG. 1 is a functional block diagram illustrating components of a projection based surgical guidance system, in accordance with an embodiment of the disclosure.

Embodiments of a system, apparatus, and method of operation for a projection based surgery guidance system are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments of this disclosure include a projection based surgical guidance system that overlays the surgical field with secondary modality imaging in a manner that aids or guides the medical practitioner (e.g., surgeon). For example, the patient may receive a fluorescent dye (e.g., ICG, methylene blue, OTL38, EC17, etc.) prior to or during a surgical procedure, intravenously, orally, or locally. A primary modality camera (e.g., color camera or grayscale camera, often stereoscopic) and a fluorescence camera are then used to image the surgical field in real time.

The camera system may use a single broad-spectrum camera with modality filters, which eases registration between the different modality images. Alternatively, the camera system may include distinct primary and secondary modality cameras along with image recognition of anatomical structures and/or identification of fiducial markers for image registration purposes. In yet another embodiment, an optical arrangement can enable two distinct cameras to have the same vantage point, magnification, and field of view to simplify image registration.

The various modality images from the camera system are fed to a controller that generates a surgical guidance image based on one or more of the modality images. For example, the surgical guidance image may include a fluorescence image that highlights or otherwise identifies tumor sites and/or various anatomical structures. The surgical guidance image is fed to a projection system that displays the surgical guidance image as a visible overlay on the surgical field, properly registered. The projection system can be combined with the camera system, or it can be a separate system. For example, the projection system and the camera system may be mounted on one or more moveable armatures that can be manipulated over a patient to view and project onto the surgical field of the patient.

Alternatively, the projection system and the camera system may be mounted on a head wearable device to be worn on the head of the medical practitioner. When worn on the head of a medical practitioner, the projection system may include a see-through head-mounted display. In this case, imagery displayed on the see-through head-mounted display is modified in accordance with the wearer's head position and head orientation such that it appears to the wearer as if it was projected as a visible overlay on the surgical field, but is invisible to other users. In some embodiments, the see-through head-mounted display includes optics to place the imagery at an optical distance equivalent to the distance from the wearer's head to the surgical field. In some embodiments, in which the modality images include three-dimensional images, the see-through head-mounted display is fitted with separate image inputs for each of the left and right eyes. In this system the projected imagery is perceived by the wearer in three dimensions.

In an open surgery scenario, the secondary modality image can be projected directly on exposed anatomical structures within the patient's body. The surgical guidance image may further include identification overlays (e.g., organ images, shape traces of anatomical structures, annotations, procedural prompts, visual guidance cues, etc.) to aid the medical practitioner during the surgical procedure. In some embodiments, the identification overlays may be used by the system for automated treatment, navigation, identification, registration, and verification.

In various endoscopic internal surgical operations (e.g., laparoscopy and thoracoscopy), the surgical guidance image may combine both the primary and secondary modality images for projection directly on the patient's skin, or immediately above on a semi-transparent screen. This exterior projection can create a visualization that is registered with the surgeon's hand and tool motions that manipulate the end of the endoscope.

The projection based solutions disclosed herein allow the medical practitioner to have direct access to the surgical field while staying focused on the surgical field and the task at hand. The medical practitioner doesn't have to switch back and forth between looking at the surgical field and looking at a screen. The orientation of the projected surgical guidance image is natural and lines up with the actual task. This avoids the need to translate actions at the fingertips to actions on a screen facing another direction. This increases the precision of the procedure, reduces the medical practitioner's reaction time, and decreases the overall procedure time. For example, if a fluorescence image identifies cancerous cells, some of them can be very small in size (<1 mm). By projecting the surgical guidance image to highlight these cancerous cells directly on the affected anatomical structures, the likelihood the medical practitioner will locate the cancerous cells and accurately remove them is increased. Furthermore, all medical team members who can view the surgical field can also view the projected surgical guidance image, accurately registered from their point of view. Due to the inherent alignment from projecting directly on the anatomical structures within the surgical field, this image guidance system is more natural and has a lower learning curve of performing image guided-surgery than conventional techniques.

FIG. 1 is a functional block diagram illustrating components of a projection based surgical guidance system 100, in accordance with an embodiment of the disclosure. The illustrated embodiment of surgical guidance system 100 includes a controller 105, one or more projectors 110, a camera system 115, a tracking system 120, user interface(s) 125, and communication interface(s) 130. The illustrated embodiment of camera system 115 includes primary modality camera(s) 135 and secondary modality camera(s) 140. The illustrated embodiment of controller 105 includes one or more processors 145 and a data store 150. The illustrated embodiment of data store 150 stores image acquisition module(s) 155, image recognition module(s) 160, registration module(s) 165, display module(s) 167, utility module(s) 170, interface module(s) 175, and procedure module(s) 180. It should be appreciated that one or more of the components illustrated in FIG. 1 are optional and need not be present in all embodiments.

Controller 105 is interconnected with the other components of surgery guidance system 100 to control and choreograph their interactions. Processor(s) 145 controls the operation of surgery guidance system 100 via the execution of logic within data store 150. The modules 155-180 may be implemented as software logic (e.g., executable software code), firmware logic, hardware logic, or various combinations thereof. Processor(s) 145 may include one or more general processing units, graphical processing units, application specific integrated circuits, or otherwise.

Projector(s) 110 may be implemented as one or more full color projectors, such as digital light processing ("DLP") projectors, liquid crystal display ("LCD") projectors, light emitting diode ("LED") projectors, etc. In other embodiments, projector(s) 110 may be implemented as single or multi-color laser projectors. Various embodiments may include a single projector for projecting an image from a single vantage point, or multiple offset projectors for displaying an image from multiple vantage points. A multi-projector system may improve projections onto three-dimensional anatomical structures and reduce image obstructions from the medical practitioner's hands or tools. As described above, when the projection system is a binocular wearable head mounted display, the three-dimensional imagery visible to the wearer may appear to conform to 3D anatomical structures.

Camera system 115 is illustrated as including two camera modalities: primary modality camera 135 and secondary modality camera 120. Primary modality camera 135 may be implemented as a full color or grayscale camera for acquiring visual images of a surgical field in real time. Camera 135 and 140 may each be a single monocular camera or implemented as a stereoscopic vision system to acquire depth perception images. Secondary modality camera(s) 140 may be implemented by a variety of different imaging systems or filters. For example, secondary modality camera(s) 140 may be one or more of a fluorescence camera, an ultrasound imager, a hyper-spectral imager, a speckle imager, an x-ray camera, a radiation imager (e.g., scintillation camera), or other medical imagers. Again, secondary modality camera(s) 140 may operate to capture secondary modality images for real time processing, registration, and re-imaging by controller 105 and projector 110.

Tracking system 120 is an optional component, which may be used in connection with various endoscopic procedures to track the position of the endoscope within the body cavity of the patient. Tracking system 120 may be implemented with known telemetry, triangulation, or imaging techniques. With precise internal position data of the end point of an endoscope, controller 105 can use projector 110 to display not only the image acquired by the endoscope within the body cavity but also its position below the skin. This image and position data can then be projected directly onto the patient's skin or surgical drapes directly above the actual position of the endoscope. Alternatively, the endoscope position data can be used to modify the perspective display parameters of the endoscopic image data projected onto the patient's skin. This technique may be useful for both laparoscopy and thoracoscopy procedures.

User interface(s) 125 may include a variety of systems to facilitate user interaction with surgery guidance system 100. For example, user interfaces 125 may include a traditional keyboard, mouse, and computer screen for both intraoperative and preoperative interactions, programming, and loading of pre-operative diagnostic images. User interfaces 125 may further include a microphone for receiving voice commands, camera system 115 for receiving gesture commands, a foot pedal for manipulation by the medical practitioner, or otherwise.

Communication interfaces 130 are provided to facilitate intercommunication between the components of surgery guidance system 100 and exterior devices. For example, communication interfaces 130 may include known wired data buses (e.g., USB, Ethernet, etc.) and wireless interfaces (e.g., Bluetooth, WiFi, etc.). In some embodiments, one or more functional components of surgery guidance system 100 may be remotely located or cloud-based. In a cloud-based architecture, processing may occur remotely and the results (e.g., secondary modality images) uploaded into the local instance of controller 105.

Figure 2:
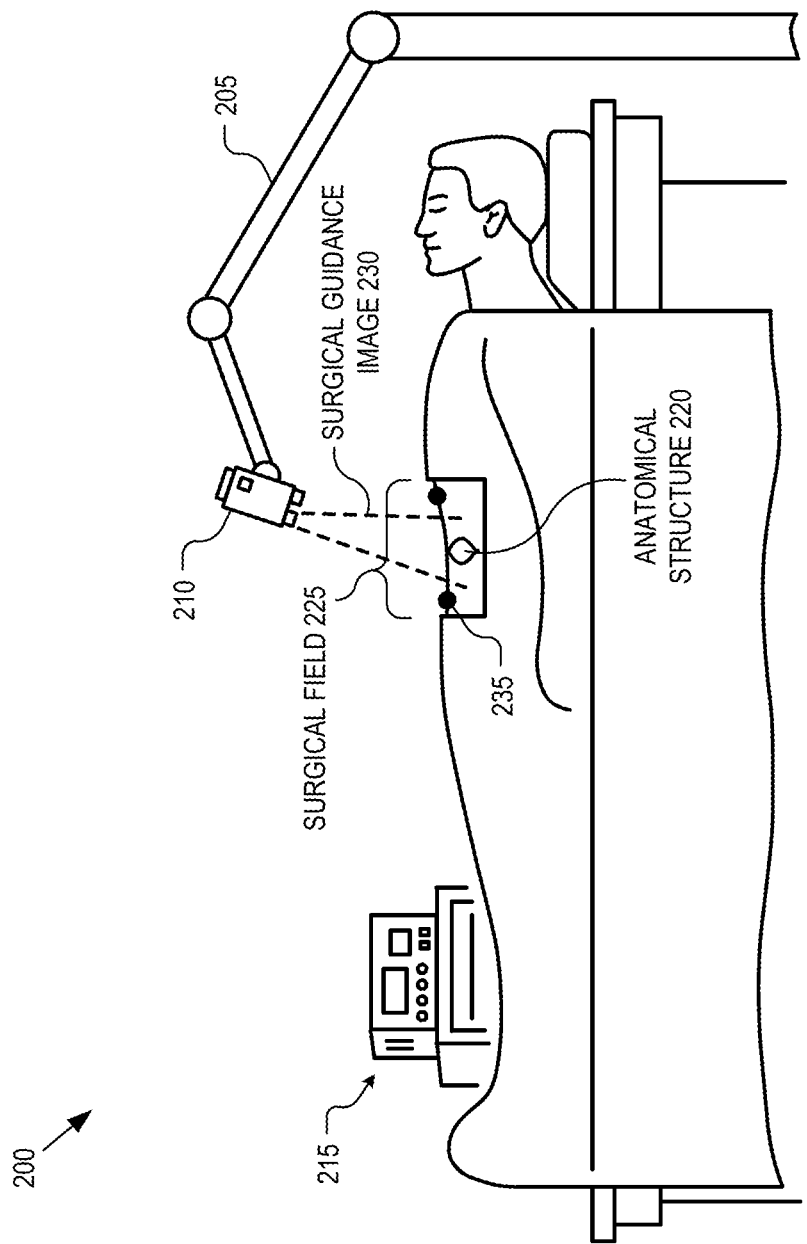
FIG. 2 is an illustration of a surgical environment for using a surgical guidance system, in accordance with a first embodiment of the disclosure.
Figure 3:
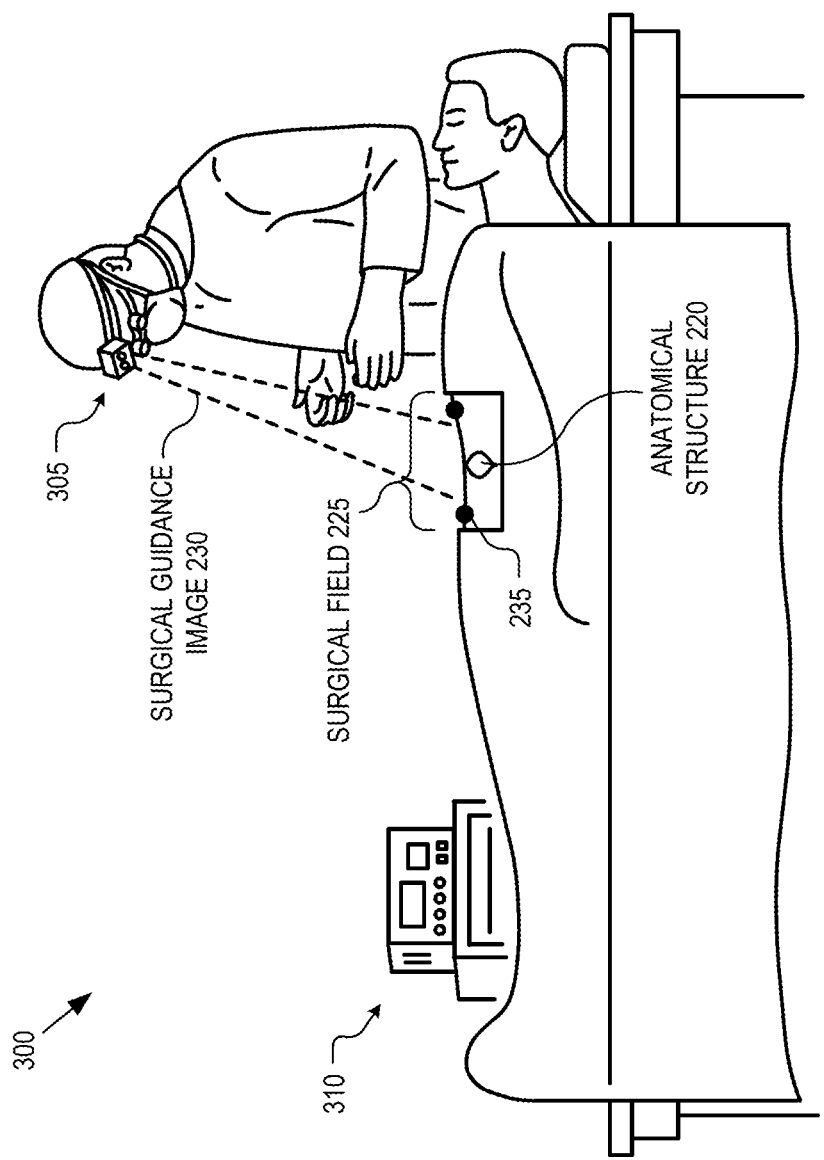
FIG. 3 is an illustration of a surgical environment for using a surgical guidance system, in accordance with a second embodiment of the disclosure.

FIGS. 2 and 3 illustrate various implementations of surgery guidance system 100. FIG. 2 is an illustration of a surgical environment 200 where components of surgery guidance system 100 are mounted to a repositionable armature 205. For example, projector 110 and camera system 115 may be integrated into head unit 210, while controller 105 may be integrated into control unit 215 with communication interfaces 130 providing the communicative interconnection. Although FIG. 2 illustrates armature 205 as being positioned on the floor, in other embodiments, armature 205 may be ceiling mounted. Alternatively, FIG. 3 is an illustration of a surgical environment 300 wherein components of surgery guidance system 100 are integrated into a head wearable device 305. For example, projector 110 and camera system 115 may be integrated into head wearable device 305, while controller 105 may be integrated into control unit 310 with communication interfaces 130 providing the communicative interconnection. Hybrid embodiments, may integrate components into both head wearable device 305 and head unit 210.

During operation, camera system 115 captures one or more real time images of anatomical structures 220 within surgical field 225. These real time images may include both primary and secondary modality images. Alternatively, or additionally, pre-operative images may also be acquired and loaded into the controller 105 for reference and analysis. Projector 110 then projects surgical guidance image 230 directly onto the patient in surgical field 225. In some embodiments, fiducial markers 235 may also be positioned to aid registration between primary modality images and one or more secondary modality images.

Figure 4:
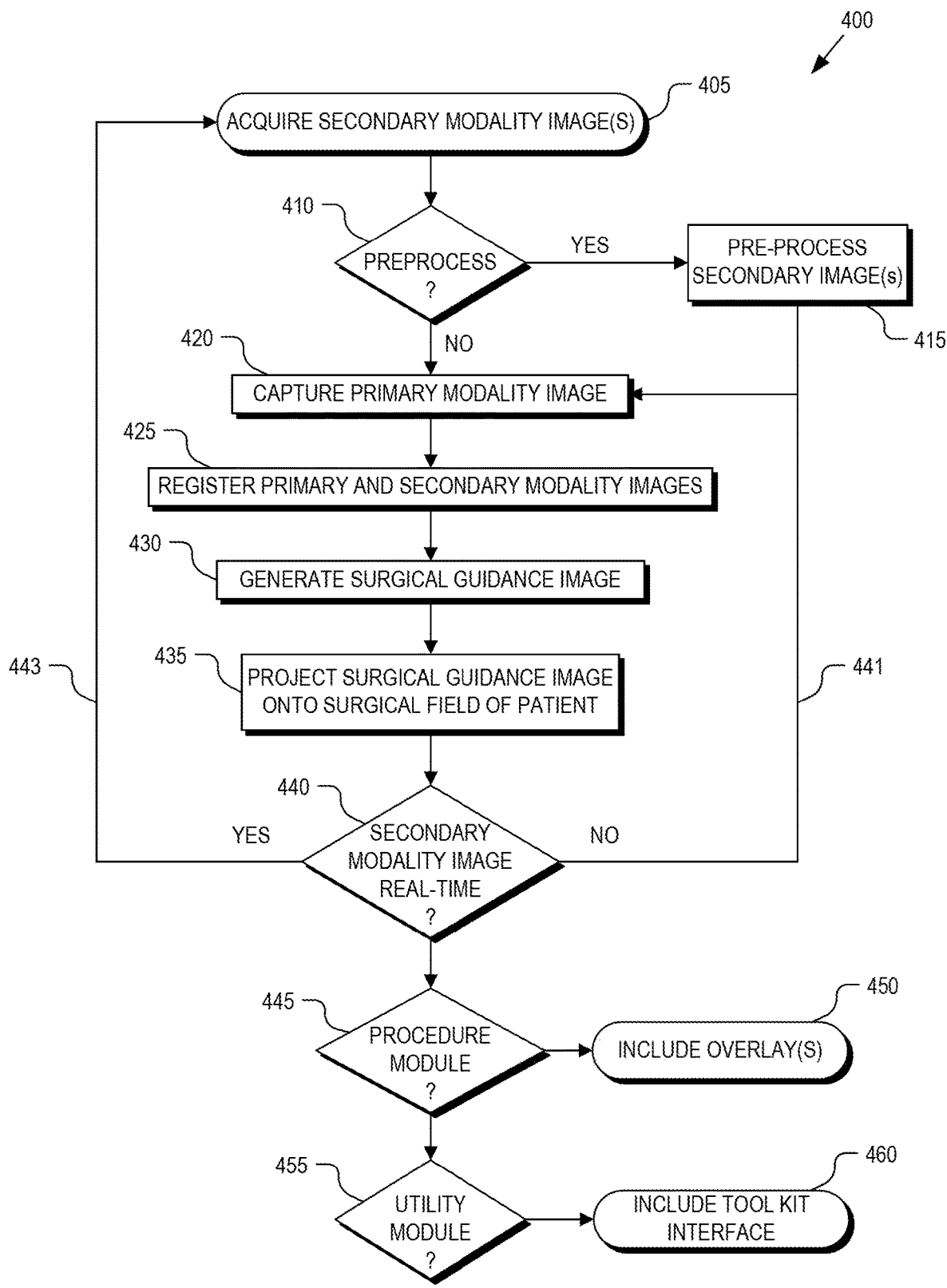
FIG. 4 is a flow chart illustrating a process of operation of a surgical guidance system, in accordance with an embodiment of the disclosure.

FIG. 4 is a flow chart illustrating a process 400 for operation of surgical guidance system 100, in accordance with an embodiment of the disclosure. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

In a process block 405, surgery guidance system 100 acquires one or more secondary modality images of surgical field 225. The secondary modality image may be a pre-operative image (e.g., MM, X-ray, CT scan, etc.) loaded into controller 105 in advance of the surgical procedure. The secondary modality image may also be an intra-operative image acquired in real time by one or more secondary modality cameras 140. In some instances, a combination of both pre-operative and intra-operative secondary modality images may be used. Real time intra-operative images may include various modalities, such as a fluorescence image, an ultrasound image, a hyper-spectral image, a speckle image, an x-ray image, a Cherenkov image, a radiation image captured by a scintillator, or otherwise. In the example of a fluorescence image, a fluorescence dye (e.g., ICG, methylene blue, OTL38, EC17, etc.) may be introduced into the patient either locally, orally, or intravenously before and/or during the procedure. Similarly, in the example of a radiation image, a radioactive tracer may be introduced into the patient before and/or during the procedure. Secondary modality images may be still pictures or live video feeds.

In some instances, pre-processing of the secondary modality image may be necessary or desirable. This preprocessing may convert the file format from one format to another, extract pertinent data, accentuate, locate, identify, or refine image features, warp or register features to a conventional atlas/orientation, or otherwise. Accordingly, if pre-processing is to be executed (decision block 410), then process 400 continues to process block 415 to execute the image processing algorithms. Otherwise, process 400 continues directly to a process block 420.

In process block 420, the primary modality image of surgical field 225 is captured by primary modality camera 135. In various embodiments, the primary modality images may be virtually any image modality, but typically will be a color image (e.g., RGB image) or a grayscale image captured intra-operatively in real time. In one embodiment, two distinct and physically offset cameras are used to acquire stereoscopic images containing depth information. Having multiple vantage points can also improve the visualization of 3D anatomical structures and reduce visual blockages from the medical practitioner's hands/surgical instruments. The acquisition and optional pre-processing of the primary and secondary images are performed by processor(s) 145 executing image acquisition module(s) 155. The images may be conveyed to processor(s) 145 via communication interface(s) 130.

Once both primary and secondary modality images have been acquired, the multiple modality images are registered to each other (process block 425). Registration may include x and y translations in the scenario of 2D images or x, y, and z translations in the scenarios of 3D images to align common features between the images. Registration may further include various rotations and even warping, if non-rigid deformations are desired. Additionally, image registration may include scaling or magnification adjustments to achieve feature size continuity between the images. In one embodiment, registration is executed via identifying common high contrast anatomical features in both images and mapping their boundaries to achieve alignment. In some embodiments, fiducial markers 235 may be introduced into both images to facilitate the registration process. This feature identification may be performed using the services of image recognition module(s) 160.

Once the multi-modal images have been scaled and/or registered by registration module(s) 165, display module(s) 167 can generate and render surgical guidance image 230 (process block 430). Surgical guidance image 230 may include just the secondary modality image, just the primary modality image, or a combination of the secondary modality image rendered as an overlay on the primary modality image. In various embodiments, or various operating modes of a single embodiment, multiple secondary modality images may be included within surgical guidance image 230 as independent overlays. Each overlay may be independently selected, or multiple overlays selected and displayed together. For example, each modality overlay may be rendered in a distinctive way (e.g., different color). As is discussed in further detail below, surgical guidance image 230 may include various graphical user interfaces and overlays for visualizing and/or distinguishing between anatomical structures, annotating anatomical structures, or prompting/guiding the medical practitioner.

Once generated, surgical guidance image 230 is projected directly onto the surgical field 225 of the patient (process block 435). In the example of open surgery, surgical guidance image 230 is projected directly onto the internal anatomical structures themselves. In the example of an endoscopic procedure, surgical guidance image 230 may be projected directly onto the patient's skin above surgical field 225 or on a semi-transparent screen drawn horizontally over surgical field 225 immediately above the patient. When projector is a see-through head-mounted display, surgical guidance image 230 is displayed to the wearer such that it appears superimposed on surgical field 225. In such an embodiment, process blocks 430 and/or 435 may include using position and orientation information from sensors built into the see-through head-mounted display to compute the projected surgical guidance image 230.

If only the primary modality image is a real time or live image feed (decision block 440), then process 100 returns to process block 420 along loop 441. However, if both the primary and secondary modality images are captured intraoperatively (decision block 440), then process 100 returns to process block 405 along loop 443.

In one embodiment, projector(s) 110 are capable of displaying surgical guidance image 230 using polarized light and the medical practitioner can wear polarized glasses that allow him/her to see different overlays with each eye. For example, surgical guidance image 230 may be generated with two independent overlays (e.g., a primary modality image overlay and a secondary modality image overlay) each projected using an orthogonal polarization. In this manner, the medical practitioner can simultaneously see both image overlays with both eyes open, or see just a single image overlay by closing the appropriate eye.

In some embodiments, surgery guidance system 100 is programmed to generate and project surgical guidance image 230 in real time based upon images acquired by camera system 115. However, in some cases, the medical practitioner's hands or instruments may temporarily obscure surgical field 225. Accordingly, in one embodiment, display module 167 may continue to project one or more overlay images for a finite period of time even though the real time image acquisition from secondary modality camera 140 has been blocked. If the secondary modality image is reacquired prior to expiration of the time period, then projection of surgical guidance image 230 continues uninterrupted. Otherwise, the image overlay that is based upon the lost secondary modality image may be discontinued or a warning provided to indicate to the medical practitioner that the image data may be stale. In some embodiments, the medical practitioner may manually select how long an image overlay is displayed in a persistent manner (e.g., 1 sec, 5 sec, 10 sec, etc.) before being refreshed or terminated.

Figure 5A:
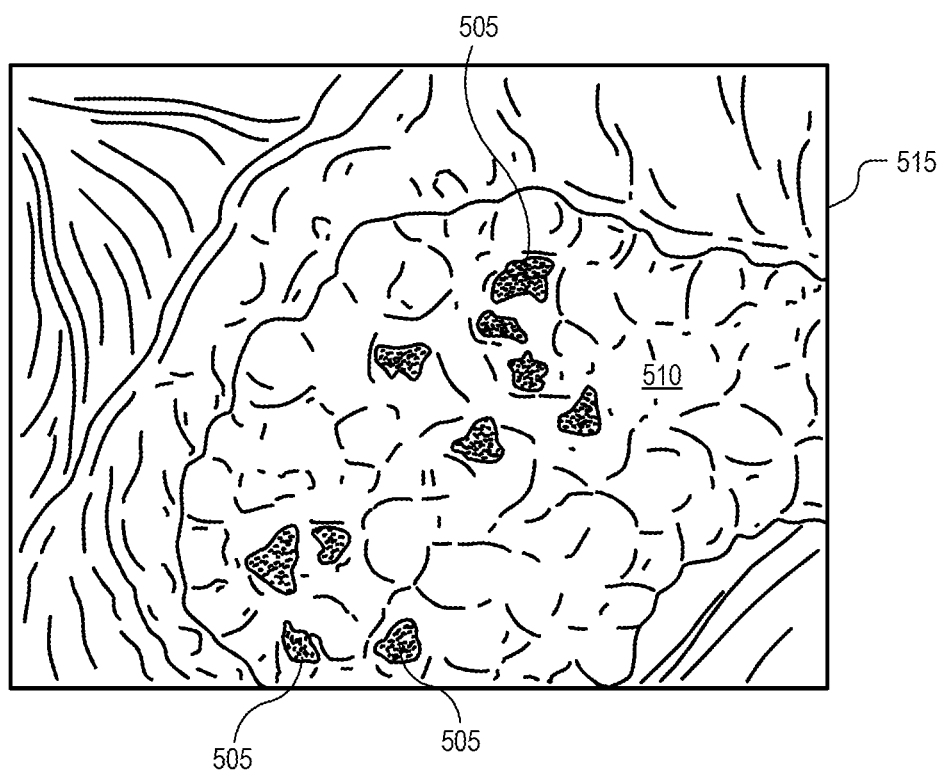
FIG. 5A is an illustration of a surgical guidance image projected onto a surgical field of a patient for identifying tumor locations on anatomical structures, in accordance with an embodiment of the disclosure.
Figure 5B:
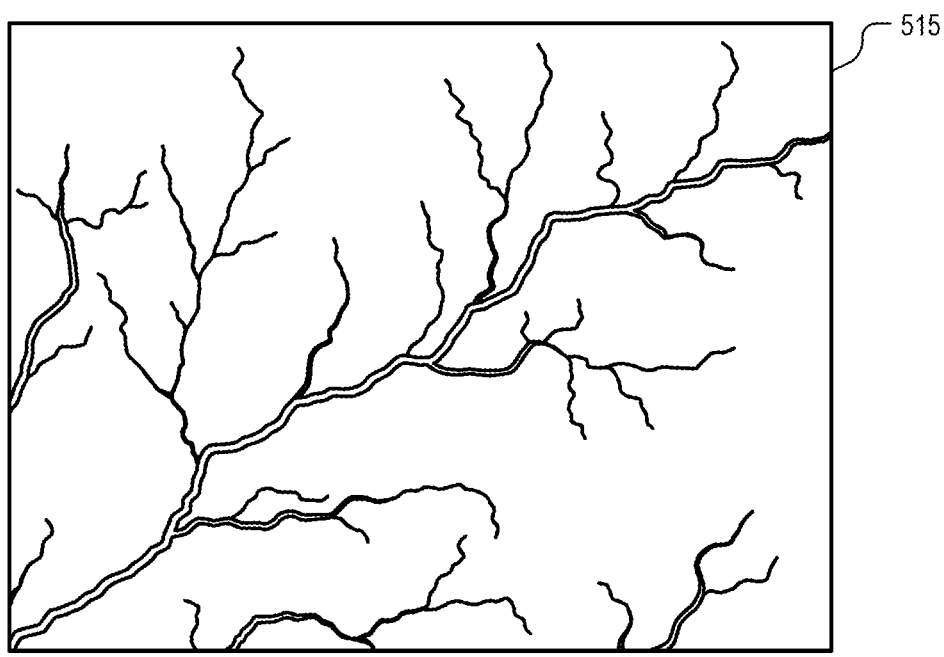
FIG. 5B is an illustration of a surgical guidance image projected onto surgical field of a patient for identifying anatomical structures, in accordance with an embodiment of the disclosure.
Figure 5C:
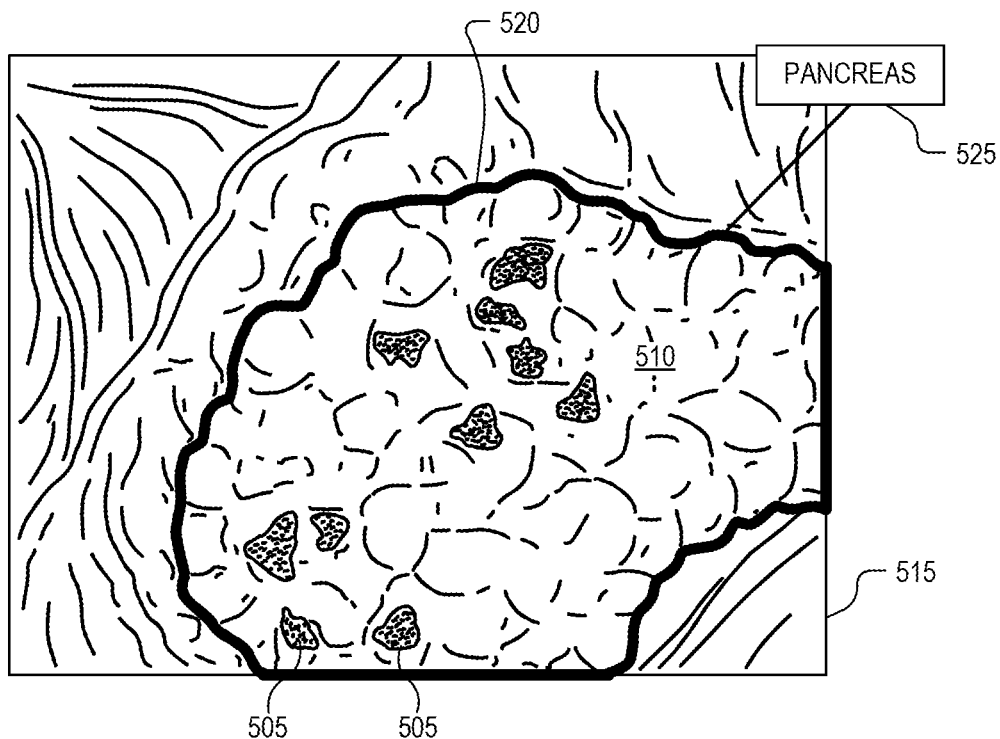
FIG. 5C is an illustration of an identification overlay included within a surgical guidance image, in accordance with an embodiment of the disclosure.

Surgery guidance system 100 may include a number of utilities and procedure applications for aiding and guiding the medical practitioner during the course of a medical procedure. For example, surgery guidance system 100 may include one or more procedure modules 180 (decision block 445) or utility modules 170 (decision block 455). Procedure modules 180 are smart applications that include procedure related overlays and logic. For example, FIG. 5A illustrates an example where the secondary modality image is projected as a fluorescence image overlay that fluorescently labels cancerous cells 505 on an anatomical structure 510 within surgical field 515. The procedure modules 180 may further include identification overlays that identify one or more anatomical structures within a surgical field. For example, FIG. 5C illustrates an identification overlay that identifies a boundary 520 of anatomical structure 510 with a shape trace. Such structures may include organs, bones, arteries (see FIG. 5B), surgical planes (e.g., the connective tissue between organs), etc. The identification overlay can aid the medical practitioner to identify and distinguish relevant anatomical structures. For example, FIG. 5 illustrates how arteries can be traced or outlined using an identification overlay to accentuate their structure. Furthermore, the identification overlay may enable annotations 525 for labeling the various anatomical structures. The annotations or labels may be automated using image recognition techniques along with knowledge of the particular procedure being performed, or manual with user input. Procedure module(s) 180 may further generate sequential prompts or cues that are tailored to specific surgical procedures. These visual guidance cues may be selected from catalog of visual guidance cues indexed to surgical procedures.

Figure 5D:
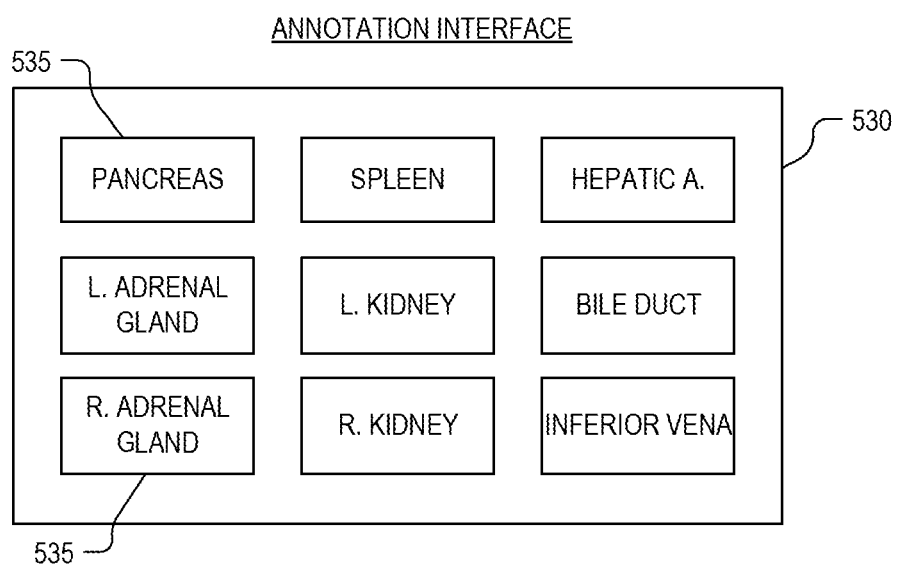
FIG. 5D is an illustration of an annotation interface that is projected adjacent to the surgical field to facilitate user interaction with the surgical guidance image, in accordance with an embodiment of the disclosure.

Utility modules 170 include miscellaneous utility logic. Utility modules 170 may include various plugins that provide augmented feature sets. For example, FIG. 5D is an illustration of an annotation interface 530 that is projected adjacent to surgical field 515 to facilitate user interaction with surgical guidance image 230, in accordance with an embodiment of the disclosure. Annotation interface 530 may display a number of anatomical labels 535 that are relevant to a particular procedure. In one embodiment, the medical practitioner may interact with annotation interface 530 using gesture commands to drag and drop labels onto various anatomical structures within surgical field 515. Additionally, or alternatively, voice commands, foot pedals, or other inputs devices may be provided to facilitate user interaction. These user interface devices are controlled by interface module(s) 175.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method for image-guided surgery, comprising:
generating instructions with a surgical guidance system comprising a controller communicatively coupled to a camera system to capture a primary modality image of a surgical field with the camera system, wherein the camera system includes an endoscope camera to capture at least the primary modality image as an internal image of a patient;
obtaining a secondary modality image of the surgical field;
generating a surgical guidance image based at least in part upon the secondary modality image, wherein the secondary modality image is registered to the primary modality image; and
generating instructions with the surgical guidance system to project the surgical guidance image from a projector onto the surgical field, wherein the surgical guidance image presents visual augmentations directly over one or more anatomical structures in the surgical field, wherein the surgical guidance image is projected with an identification overlay that automatically identifies and labels the one or more anatomical structures based upon registration, by the controller, of the secondary modality image to the primary modality image.

2. The method of claim 1, wherein the surgical guidance image indicates, by discontinuing the secondary modality image or by providing a separate warning within the surgical guidance image, if the secondary modality image ceases to be registered to the primary modality image.

3. The method of claim 1, further comprising tracking a position of the endoscope camera within a body cavity of the patient,
wherein the surgical guidance image includes a visual indication, projected on or over the patient, of the position of the endoscope camera within the body cavity of the patient, and
wherein a location of the visual indication of the position of the endoscope camera moves within the surgical guidance image based at least in part upon the position of the endoscope camera within the body cavity of the patient.

4. The method of claim 1, further comprising:
generating instructions with the surgical guidance system to capture the secondary modality image with the camera system in real time during the surgical procedure by the camera system, wherein the secondary modality image is different from the primary modality image and comprises at least one of a fluorescence image from a fluorescent dye, an ultrasound image, a hyper-spectral image, a speckle image, an x-ray image, a Cherenkov image, or a radiation image from a radioactive tracer.

5. The method of claim 1, wherein the secondary modality image comprises a pre-operative image of the surgical field acquired prior to the surgical procedure using a second imaging modality that is different than a first imaging modality used to capture the primary modality image.

6. The method of claim 1, further comprising:
registering multiple secondary modality images of the surgical field to the primary modality image, wherein each of the multiple secondary modality images is acquired using a different imaging modality;
generating multiple surgical guidance images based at least in part upon the multiple secondary modality images; and
generating instructions with the surgical guidance system to project the multiple surgical guidance images, each with a different color or a distinct appearance, onto the surgical field.

7. The method of claim 1, wherein the generating instructions to capture the primary modality image, the generating the surgical guidance image, and the generating instructions to project the surgical guidance image are performed in real time during the surgical procedure such that the surgical guidance image tracks movements of the one or more anatomical structures.

8. The method of claim 1, wherein the position of the endoscope camera is at least partially determined by registering the primary modality image with the secondary modality image in real time.

9. The method of claim 1, further comprising registering the secondary modality image to the primary modality image with the surgical guidance system prior to generating the surgical guidance image.

10. At least one non-transitory machine-readable medium storing instructions that, when executed by a machine, will cause the machine to perform operations for image-guided surgery, comprising:

generating instructions with a surgical guidance system comprising a controller communicatively coupled to a camera system to capture a primary modality image of a surgical field with the camera system, wherein the camera system includes an endoscope camera to capture at least the primary modality image as an internal image of a patient;

obtaining a secondary modality image of the surgical field;

generating a surgical guidance image based at least in part upon the secondary modality image, wherein the secondary modality image is registered to the primary modality image; and generating instructions with the surgical guidance system to project the surgical guidance image from a projector onto the surgical field, wherein the surgical guidance image presents visual augmentations directly over one or more anatomical structures in the surgical field, wherein the surgical guidance image is projected with an identification overlay that automatically identifies and labels the one or more anatomical structures based upon registration, by the controller, of the secondary modality image to the primary modality image.

\* \* \* \* \*